(12) United States Patent
Smidt

(10) Patent No.: US 10,946,304 B2
(45) Date of Patent: Mar. 16, 2021

(54) PROCESS FOR RECOVERING ALDEHYDE OBTAINED BY HYDROFORMULATION IN TWO COLUMNS WITH INCREASING PRESSURE

(71) Applicant: JOHNSON MATTHEY DAVY TECHNOLOGIES LIMITED, London (GB)

(72) Inventor: Martin Lucas Smidt, London (GB)

(73) Assignee: Johnson Matthey Davy Technologies Limited, London (GB)

( * ) Notice: Subject to any disclaimer, the term of this patent is extended or adjusted under 35 U.S.C. 154(b) by 233 days.

(21) Appl. No.: 16/086,189

(22) PCT Filed: Jan. 30, 2017

(86) PCT No.: PCT/GB2017/050234
§ 371 (c)(1),
(2) Date: Sep. 18, 2018

(87) PCT Pub. No.: WO2017/158315
PCT Pub. Date: Sep. 21, 2017

(65) Prior Publication Data
US 2020/0298138 A1 Sep. 24, 2020

(30) Foreign Application Priority Data
Mar. 18, 2016 (GB) .................. 1604608

(51) Int. Cl.
*B01D 3/14* (2006.01)
*B01D 53/14* (2006.01)
*C07C 45/80* (2006.01)
(52) U.S. Cl.
CPC ......... *B01D 3/143* (2013.01); *B01D 53/1487* (2013.01); *C07C 45/80* (2013.01)

(58) Field of Classification Search
CPC ...... B01D 3/143; B01D 53/1487; C07C 45/80
See application file for complete search history.

(56) References Cited

U.S. PATENT DOCUMENTS 3,692,634 A * 9/1972 Othmer .................. B01D 3/065
203/11
4,210,426 A 7/1980 Sridhar
(Continued)

FOREIGN PATENT DOCUMENTS

CN 1085651 C 4/1994
CN 104784958 A 7/2015
(Continued)

OTHER PUBLICATIONS

PCT/GB2017/050234 International Search Report dated Mar. 21, 2017.
(Continued)

*Primary Examiner* — Jonathan Miller
(74) *Attorney, Agent, or Firm* — BakerHostetler

(57) ABSTRACT

A process for the separation of an aldehyde and a second component from a feed stream (3a, 3b, 3c) comprising the aldehyde and the second component, said process comprising: providing the feed stream to one or both of a first separation vessel (1) operating at a first pressure and a second separation vessel (2) operating at a second pressure wherein said second pressure (2) is greater than said first pressure; operating said first separation vessel (1) and said second separation vessel (2) such that separation occurs; recovering an aldehyde product stream (4) from at or near the bottom of the first separation vessel (1), said aldehyde product stream (4) having a concentration of aldehyde which is higher than that in the feed stream (3a, 3b, 3c); recovering a second component stream (8) from at or near the top of the second separation vessel (2), said second component stream having a concentration of second component which is higher (Continued)

than in the feed stream (3*a*, 3*b*, 3*c*); removing a first recycle stream (5, 6) from at or near the top of the first separation vessel (1) and feeding it to the second separation vessel (2); and removing a second recycle stream (9, 10) from at or near the bottom of the second separation vessel (2) and feeding it to the first separation vessel (1).

20 Claims, 4 Drawing Sheets

(56) References Cited

U.S. PATENT DOCUMENTS

| | | | | |
|---|---|---|---|---|
| 4,277,268 | A | * | 7/1981 | Spangler, Jr. ........ B01D 1/2856 203/24 |
| 4,360,405 | A | * | 11/1982 | Tsao ................... B01D 1/2846 203/24 |
| 4,479,012 | A | | 10/1984 | Fischer et al. |
| 4,496,781 | A | * | 1/1985 | Jacobson ................ B01J 31/24 568/462 |
| 4,718,986 | A | * | 1/1988 | Comiotto ................ C07C 7/005 203/26 |
| 5,001,274 | A | * | 3/1991 | Bunning ................ C07C 45/50 568/454 |
| 5,087,763 | A | | 2/1992 | Sorenson |
| 5,294,304 | A | * | 3/1994 | Kano ..................... C07C 29/84 203/19 |
| 5,463,137 | A | | 10/1995 | Ramachandran et al. |
| 5,516,965 | A | | 5/1996 | Hershkowitz et al. |
| 5,675,041 | A | * | 10/1997 | Kiss ..................... C07C 45/50 568/454 |
| 6,511,583 | B1 | * | 1/2003 | Muller .................. C07C 45/50 203/78 |
| 6,822,122 | B2 | | 11/2004 | Richter et al. |
| 6,969,777 | B2 | | 11/2005 | Walz et al. |
| 9,851,140 | B2 | * | 12/2017 | Wakabayashi ......... F25J 1/0022 |
| 10,016,699 | B2 | * | 7/2018 | Wakabayashi ......... B01D 3/143 |
| 2003/0176743 | A1 | | 9/2003 | Walz et al. |
| 2006/0058538 | A1 | | 3/2006 | Haderlein et al. |
| 2013/0213792 | A1 | | 8/2013 | Wakabayashi et al. |
| 2015/0202547 | A1 | * | 7/2015 | Wakabayashi ......... B01D 3/007 202/161 |

FOREIGN PATENT DOCUMENTS

| | | |
|---|---|---|
| DE | 102007004788 A1 | 8/2008 |
| EP | 2896442 A1 | 7/2015 |
| JP | H0840966 A | 2/1996 |
| WO | WO 2008/092575 A1 | 8/2008 |

OTHER PUBLICATIONS

PCT/GB2017/050234 Written Opinion dated Mar. 21, 2017.
GB1604608.8 Search Report Under Section 17(5) dated Oct. 26, 2016.
GB1701507.4 Combined Search and Examination Report Under Sections 17 and 18(3) dated Jul. 20, 2017.

* cited by examiner

PROCESS FOR RECOVERING ALDEHYDE OBTAINED BY HYDROFORMULATION IN TWO COLUMNS WITH INCREASING PRESSURE

CROSS-REFERENCE TO RELATED APPLICATIONS

This application is the National Stage of International Patent Application No. PCT/GB2017/050234, filed Jan. 30, 2017, which claims priority from Great Britain Patent Application No. 1604608.8, filed Mar. 18, 2016, the disclosures of each of which are incorporated herein by reference in their entireties for any and all purposes.

The present invention relates to the process for the separation of two or more components from a mixture where temperature sensitivities restrict viable operating temperature ranges for the separation. More specifically, the present invention relates to a process for the separation of an aldehyde from the olefin from which the aldehyde has been produced in a hydroformylation reaction. The alkane corresponding to the olefin may also be present and need to be separated. The present invention is particularly suitable for the separation of butyraldehyde from propylene optionally with propane, the separation of valeraldehyde from butylene optionally with butane, and the separation of propionaldehyde from ethylene optionally with ethane. The present invention is also suitable for the separation of an aldehyde from other compounds including, for example, the corresponding unsaturated aldehyde from aldol condensation.

The need to separate two or more components from a mixture is an issue which has been considered for many years. Whilst various separation methods such as distillation are known and effectively used, there are still problems associated with some separations, particularly where the sensitivity to temperature of one or more of the components present in the mixture restricts the viable operating temperatures which can be used for the separation.

One separation process which suffers from restrictions imposed by the required operating temperatures is that of separating an aldehyde formed by hydroformylation from the olefin from which it has been formed. This mixture requiring separation may additionally include the alkane corresponding to the olefin since the olefin supplied to the hydroformylation reaction will generally contain some alkane. Thus in one example, the separation may be of butyraldehyde from propylene and optionally propane. Where there is complete conversion of the olefin, there will still generally be a requirement to separate the aldehyde from alkane present. Thus in one example, the separation may be of butyraldehyde from propane. The product stream from the hydroformylation reactor from which the butyraldehyde has to be separated will generally also include synthesis gas, as well as inerts such as nitrogen, carbon dioxide and argon and thus there have to be considered when formulating a separation scheme.

Hydroformylation reactions such as the formation of butyraldehyde from propylene are conventionally carried out using a rhodium catalyst with a triphenylphosphine ligand. This is commonly operated with a limited single pass conversion at about 80 to 90%. It is believe that the catalyst complex is stabilized by the presence of the propylene. Thus, at conversions close to 100%, as the propylene concentration drops towards zero, the catalyst complex becomes less stable which may result in high rhodium losses which in turn impact on the economics of the process. In order to improve the economics, any unconverted propylene leaving the reactor in the product stream needs to be recovered and recycled to the reactor.

Other ligands such as phosphites may be used in the catalyst, Whilst these may be more stable in the absence of propylene and so may allow for a single pass conversion closer to 100%, they too have problems associated with their use. This is because the rate of hydroformylation is approximately proportional to the propylene concentration. At a conversion rate close to 100% the propylene concentration approaches zero and thus the rate of reaction also approaches zero. This means that to achieve a high conversion a large reactor size is required which can make the process uneconomical in terms of capital and operating costs. It may therefore be necessary with conventional processes to operate at a limited single pass conversion and recover and return the unconverted propylene.

Thus not only is it desirable to separate the product aldehyde so that the desired product can be recovered, it is also desirable to recover the unreacted olefin for return to the hydroformylation reactor.

Similar issues are noted with the separation of other aldehydes from their corresponding olefins and optionally corresponding alkane and with other catalysts.

Various proposals have been made associated with the separation of product streams from hydroformylation reactions. US2003/176743 is one example of a so-called 'gas recycle' process. In this process, a gaseous stream comprising unreacted olefin, the corresponding alkane, unreacted synthesis gas and the aldehyde product is recovered from the gas space of the reactor. This is then cooled such that it is partially condensed and passed to a phase separation vessel where the gas and liquid portions are separated. The gaseous part is recycled to the hydroformylation reactor. The liquid phase, which includes the aldehyde, the unreacted olefin and the alkane dissolved therein, is fed to a degassing column from the top of which a mixture of olefin and alkane is obtained. The aldehyde product is recovered from the bottom of the degassing column. The mixture of olefin and alkane is fed to a rectification column where a portion of the alkane is separated from the olefin. The alkane produced in the rectification column can be recovered and removed from the system and the olefin can be recycled to the reactor. The degassing column is therefore effectively an olefin and alkane/aldehyde separator. Any aldehyde going overhead in the degassing column will leave the rectification column with the alkane and is thus lost. Similarly, any olefin leaving the degassing column with the aldehyde is not returned to the reactor and is therefore lost.

An alternative arrangement is discussed in U.S. Pat. No. 5,516,965. In this arrangement, a gaseous or mixed phase effluent is cooled to a temperature at which some aldehyde condenses. The liquid aldehyde is separated in a flash drum before being passed to a stripping vessel where it is stripped with an unsaturated-free gas to produce an olefin-free aldehyde product and a gaseous effluent which contains the olefin. The gaseous effluent from the stripping vessel and that from the flash drum are combined before being cooled to produce a stream which is passed to an absorption tower.

The upper portion of the absorption tower is operated at a temperature which is sufficiently low that reflux of the alkane component can occur. This upper portion functions as the rectifying section of a distillation tower, rejecting any aldehyde and resulting in a substantially aldehyde-free overhead product stream that contains inert gases from the reaction and non-stoichiometric components such as hydrogen which boil at temperatures at or below the temperature of the refluxing alkane. In the bottom of the distillation tower, the liquid phase becomes cold aldehyde that dissolves the highly soluble unsaturated components as if in an absorber. At the temperatures present in the bottom of the tower the solubilities of the olefin in the liquid phase is high. This unsaturated-containing liquid stream is removed from the bottom of the tower and is pumped as a liquid at substantially higher pressures for recycle to the reactor.

Examples of other process which address the separation of an aldehyde include those described in U.S. Pat. Nos. 4,479,012, 5,087,763, 5,001,274, 5,463,137, 6,822,122, 6,969,777, and 5,675,041.

Various proposals have also been made relating to the separation of the olefin from the corresponding aldehyde. For example in U.S. Pat. No. 4,210,426 a three-column scheme is used where the first column is a butyraldehyde scrubber, the second column is a separation column in which the butyraldehyde is separated from the propylene and propane and the third column is a propylene/propane splitter. The off-gases from the hydroformylation reactor are introduced into the centre of the first column and propylene/propane-free isobutyraldehyde is introduced at the top of the column. The propylene and propane are absorbed into the isobutyraldehyde and the non-absorbed gases are taken off at the top of the column for recycling to the hydroformylation reaction or removed from the system. The mixture of the isobutyraldehyde and propylene and propane are passed to the second column in which the propylene and propane are separated from the isobutyraldehyde which is returned to the first column. The propylene and propane are passed to the third column where they are separated by distillation.

Whilst these various processes propose potentially viable schemes to recover the desired product aldehyde they each still suffer from various disadvantages and drawbacks.

Taking as an example the separation of butyraldehyde and propylene, where these are to be separated in a distillation column a large temperature difference is required between the stream removed from the bottom of the reactor and that removed overhead in order to achieve good separation. However, the use of this large temperature difference either means that the temperature required at the bottom of the distillation column has to be very high or the overhead temperature has to be very low to achieve the desired difference and hence the separation. However, the use of a high temperature at the bottom is problematic as it leads to the formation of heavies resulting in a loss of desired product. In addition, the use of a low temperature as overhead is problematic since it will generally have to be so low that cooling water cannot be used to condense the overhead stream such that a refrigeration system will be required which is an expensive addition to the process.

A further problem with the separation of butyraldehyde and propylene relates to the presence of propane in the starting material. Once separated from the butyraldehyde, the propylene will generally be recycled to the reactor in which the aldehyde is formed. Since the propylene recycle stream will include propane, the propane will be returned with the propylene unless means to remove it are included. Propane will therefore accumulate in the reactor. As the propane accumulates it will limit the efficiency of the reactor. It is therefore also desirable to separate the propane from the propylene so that the propane is not returned to the reactor.

Similar problems are noted in connection with the separation of valeraldehyde from butylene which may include some butane and with the separation of propionaldehyde from ethylene which may include ethane and indeed with the separation from the any aldehyde produced by hydroformylation from the olefin used in its production and the corresponding alkane. In addition similar problems are noted when separating aldehydes from, for example, unsaturated aldehydes.

It is therefore desirable to provide a process which addresses at least some, and preferably all of these problems.

It has now been found that at least some of these problems may be addressed by the use of a separation process utilising two separation vessels, one operated at a low pressure and the other at a high pressure where the two vessels are linked such that there is a recycle loop between the two vessels.

Thus according to a first aspect of the present invention there is provided a process for the separation of an aldehyde and a second component from a feed stream comprising the aldehyde and the second component, said process comprising:

a) providing the feed stream to one or both of a first separation vessel operating at a first pressure and a second separation vessel operating at a second pressure wherein said second pressure is greater than said first pressure;

b) operating said first separation vessel and said second separation vessel such that separation occurs;

c) recovering an aldehyde product stream from at or near the bottom of the first separation vessel, said aldehyde product stream having a concentration of aldehyde which is higher than that in the feed stream;

d) recovering a second component stream from at or near the top of the second separation vessel, said second component stream having a concentration of second component which is higher than in the feed stream;

e) removing a first recycle stream from at or near the top of the first separation vessel and feeding it to the second separation vessel; and f) removing a second recycle stream from at or near the bottom of the second separation vessel and feeding it to the first separation vessel.

It will be understood that the first and second separating vessels are configured such that a stream recovered from at or near the bottom of the second separation vessel is passed to the first separation vessel and a stream recovered from at or near the top of the first separation vessel is passed to the second separation vessel. Thus a recycle loop is established between the first and second separation vessels.

It will be further understood that the two separation vessels operate such that the heavier component in the feed stream to the first separation vessel, is obtained from at or near the bottom of the first, lower pressure, separation vessel. The overhead stream from the first separation vessel will comprise a mixture of heavy and light components. These are sent to the second separation vessel which is operated at a higher pressure than the first. In this second separation vessel, the lighter component in the feed stream is removed as overhead from the second column and a mixture of heavy and light components is removed from the bottom and returned to the first, lower pressure separation vessel. Thus each separation vessel provides one stream of a purified component and a stream which comprises a mixture of components such that the reduced temperature difference can be used. In this connection, it will be understood that complete separation in a single vessel would require a larger temperature difference.

Having two vessels operating at different pressures allows the temperature of the bottom of the separation vessel operating at the first, lower, pressure to remain relatively low so that the production of heavy by-products is reduced and preferably avoided. Further the inclusion of a second separation vessel operated at a pressure that is higher than that in the first separation vessel allows an appropriate temperature to be used such that the stream recovered from at or near the top of the separation vessel can be condensed using cooling water rather than expensive refrigeration equipment.

Thus the present invention enables a lower temperature difference between the first component stream and the second component stream to be used than is achievable where a single separation vessel, such as a distillation column, is used. In this connection it will be understood that a conventional single separation column using cooling water would result in a higher temperature for the stream recovered from the bottom for the same level of separation.

The process of the present invention is suitable for separating any aldehyde from a stream comprising the aldehyde and other components. It is particularly suitable where the temperature sensitivities restrict viable operating temperature ranges for the separation.

In one arrangement, the second component is an olefin which may be the olefin from which the aldehyde has been formed. The feed stream comprising the aldehyde may be one recovered from a hydroformylation reaction and it will therefore include the olefin from which the aldehyde is formed in the reactor. The olefin may be a $C_2$ to $C_{20}$ olefin and the aldehyde will have one more carbon than the olefin. In one arrangement, the aldehyde is butyraldehyde and it is separated in accordance with the present invention from propylene optionally with propane. In an alternative arrangement, the aldehyde is valeraldehyde and it is separated in accordance with the present invention from butylene optionally with butane. In a further alternative arrangement, the aldehyde is propionaldehyde and it is separated in accordance with the present invention from ethylene optionally with ethane.

In a still further arrangement the aldehyde may be separated from an unsaturated aldehyde. The unsaturated aldehyde may be a $C_3$ to $C_{20}$ unsaturated aldehyde. Thus, for example, butyraldehyde may be separated from ethyl propyl acrolein which is a common intermediate in the production of 2-ethylhexanol and is produced by the aldolisation of n-butylraldehyde. Similarly, valderaldehyde may be separated from propylbutylacrolein which is a common intermediate in the production of 2-propylheptanol and is produced by the aldolisation of valeraldehyde.

The process of the present invention may also be used to separate 2-methylbutyryladeyde, 3-methylbutyrylaldehyde or both 2-methylbutyrylaldehyde and 3-methylbutyrylaldehyde from propylbutylacrolein.

However, it will be understood that the process of the present invention is not limited to the compounds detailed above and is suitable for separating any aldehyde from a mixture.

One or more aldehydes may be separated using the process of the present invention.

The feed stream may be fed to the first separation vessel or to the second separation vessel. In one arrangement, the feed stream may be fed to both separation vessels. Means may be provided for selecting whether the mixture is fed to the first separation vessel, the second separation vessel, or to both separation vessels such that switching of where the feed stream can be fed can be achieved.

In one alternative arrangement feed may be added between the first and second separation vessels. This may be as an alternative to, or in addition to, supplying feed stream directly to one or both of the first and second separation vessels.

Any suitable separation vessel may be used. The first and second separation vessels may be the same or different. For example, one or both vessels may be flash vessels with associated condensers. Particular advantages may be noted where one, or both, of the separation vessels is a separation column.

The process of the present invention may include more than two separation vessels to assist the separation of the aldehyde. Such arrangements are within the scope of the present invention provided that there is a first separation vessel having a first operating pressure and a second separation vessel having a second operating pressure which is above that of the first operating pressure and that a recycle loop is formed between these separation vessels.

Any suitable pressure may be used in the first and second separation vessels provided that the pressure in the second separation vessel is higher than that in the first separation vessel. The particular pressure selected will generally depend on the temperature requirements of the separation being carried out. Further, the pressure will generally be chosen to provide the desired temperature profile in the first and second separation vessels.

In one arrangement, the second pressure is higher than the first pressure by about 0.1 bara to about 48 bara, or from about 5 to about 45 bara.

The pressure in the second separation vessel will generally be below the critical pressure of the mixture therein.

In one arrangement, the pressure in the first separation vessel may be a vacuum of the order of about 1 mbara although pressures of about 10 to about 50 mbara may be used.

Where the process is for the separation of butyraldehyde from propylene an optionally propane, the first separation vessel may operate at a pressure of from about 0.05 bara to about 10 bara, or at a pressure of from about 1 bara to about 5 bara, or at a pressure of from about 2 bara to about 3 bara. In one arrangement, the first separation vessel may be operated at a pressure of about 2.8 bara.

The second separation vessel may operate at a pressure of from about 0.1 bara to about 30 bara, or at a pressure of from about 15 bara to about 25 bara provided that the pressure selected is above that used in the first separation vessel. Where the aldehyde being separated is butyraldehyde, the second separation vessel may be operated at a pressure of about 18 bara.

The first recycle stream will generally be in the gas phase for systems where the dewpoint of the stream recovered from at or near the top of the first separation vessel which is operated at the lower pressure is below cooling water temperature. In this connection, it will be noted that in most olefin/aldehyde systems the feed mixture will contain incondensables such as those selected from the group consisting of hydrogen, nitrogen and methane. These incondensables will go overhead in the first separation vessel and will result in a dewpoint far below the cooling water temperature.

The first recycle stream will generally be passed through one or more compressors before it is fed to the second separation vessel. The, or each, compressor may be associated with an intercooler.

In one alternative arrangement, the first recycle stream recovered from the top of the first separation vessel is a liquid. In this arrangement, the compressor will generally be replaced by a pump.

In an ideal arrangement of the present invention, the first and second separation vessels are operated such that the temperatures in both separation vessels is about the same and such that the temperature in the overhead from both separation vessels is about the same. This temperature will generally be a little above cooling water temperature.

The lower portion of the first separation vessel may be operated at any suitable temperature. In one arrangement a temperature of about 50° C. to about 200° C. or about 60° C. to about 150° C. or about 80° C. to about 130° C. may be used. Particular advantages may be noted when the lower portion of the first separation vessel is operated at about 90° C. to about 110° C.

The lower portion of the second separation vessel may be operated at any suitable temperature. In one arrangement, a temperature of about 50° C. to about 200° C. or about 60° C. to about 150° C. or about 80° C. to about 130° C. may be used. Particular advantages may be noted when the upper portion of the second separation vessel may be operated at about 90° C. to about 110° C.

The second separation vessel will generally be operated at a temperature and pressure such that the second component stream recovered from at or near the top of the second separation vessel may be condensed using cooling water such that the need for expensive refrigeration can be avoided. In addition, the first separation vessel may be operated with a temperature of the stream recovered from at or near the top of the vessel just above that of the cooling water.

The pressure may be selected such that the temperature of the stream taken from the bottom portion of the second separating vessel may be within about 20° C. of the temperature of the bottom portion of the first separating vessel. In one arrangement the temperature of the stream taken from the bottom portion of the second separating vessel is within about 10° C. of the temperature of the bottom portion of the first separating vessel.

Where the stream recovered from the separation vessels is a vapour, a condenser may be associated with one or both separation vessels as appropriate. Where the stream is a liquid, a condenser will not be required. However, the stream may still require cooling.

Where a condenser is present on the first separation vessel, the dew point of the stream taken from at or near the top of the first separation vessel is preferably higher than the temperature of the condenser associated therewith. The condensate from this condenser may be returned to the first separation vessel.

Where a condenser is present on the second separation vessel, the dew point of the stream taken from at or near the top of the second separation vessel is preferably higher than the temperature of the condenser associated therewith. The condensate from this condenser may be returned to the second separation vessel.

In one arrangement, the first recycle stream, the second recycle stream, or the first and second recycle stream may be passed through a further separation means. Any suitable further separation means may be used. In one arrangement, the further separation means may be a gas/liquid separation device.

In one arrangement, an olefin/alkane splitter may be present. In one arrangement, the olefin/alkane splitter may be located between the first and second separation vessels. In this arrangement, the stream taken from at or near the top of the first separation vessel may be passed to the olefin/alkane splitter such that the olefin and the alkane may be separated into an upper stream enriched in at least one component and a lower stream depleted in the at least one component. In one arrangement, the stream comprising the alkane will also include the aldehyde and hence it is this stream which is passed to the other separation vessel.

Additionally or alternatively, the olefin/alkane splitter may be located outside the recycle loop formed by the first and second separation vessels. In this configuration, it is generally the overhead from the second, high pressure, separation vessel that is passed to the olefin/alkane splitter. The olefin enriched stream will generally be recovered from the upper portion of the splitter. The alkane enriched stream will comprise the alkane.

The process of the present invention may also be used in processes in which water is present in the mixture to be separated. Where water is present, the stream may be passed through a water-removing means. Any suitable water-removing means may be used. Suitable means include a decanter. In this arrangement one or both phases may be used as reflux.

According to a second aspect of the present invention there is provided a process for carrying out the hydroformylation of an olefin wherein one or more vent streams from a hydroformylation reaction provides the feed stream for the above first aspect of the present invention.

In one arrangement, the stream is treated in an aldehyde scrubber against a stream which is substantially free of olefin. The stream may be cooled before it is passed to the aldehyde scrubber.

The present invention will now be described, by way of example, with reference to the accompanying figures in which.

It will be understood by those skilled in the art that the drawings are diagrammatic and that further items of equipment such as reflux drums, pumps, vacuum pumps, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

The process of the present invention will now be described by way of example with reference to the separation of butyraldehyde and propylene from a hydroformylation reaction. It will be understood that it is equally applicable to separating other aldehydes from the olefin from which they are formed in a hydroformylation reactions.

Figure 1:
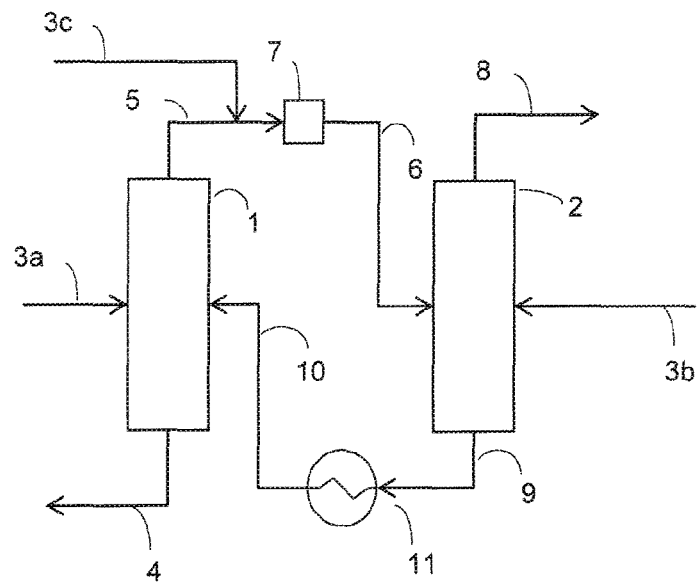
FIG. 1 is a schematic diagram illustrating the process of the present invention.

A schematic diagram illustrating the overall concept of the process of the present invention is set out in FIG. 1. The process of the present invention requires first and second separation vessels. In the illustrated arrangements these are provided by a low pressure column 1 and a high pressure column 2. Each column may be provided with a condenser, a reboiler or both a condenser and a reboiler, not shown in FIG. 1.

The feed which will comprise both a heavy component, in this example the butyraldehyde, and lighter components, in this example the propylene and optionally some alkane, propane, is added via lines 3a, 3b or 3c. Thus the feed may be supplied to either the low pressure column 1 or the high pressure column 2. Separation will occur in both columns. In some arrangements, feed may be added in more than one of lines 3a, 3b and 3c. It will be understood that more than one feed may be added at more than one position to the, or each, column and/or between the columns. Thus one or more of lines 3a, 3b and 3c may represent more than one feed line.

The heavy butyraldyde will be recovered from the bottom of the low pressure column 1 in line 4, The stream removed from the top of the low pressure column 1 in line 5 is passed in line 6 to the high pressure column 2. Usually the stream will be passed through a pump or compressor 7. This stream, which comprises a mixture of heavy and light components, is passed in line 6 to the high pressure column 2.

Further separation occurs in the high pressure column 2 and the light component is recovered from the top of the high pressure column 2 in line 8. The stream removed from the bottom of the high pressure column 2 in line 9 is passed to the low pressure column 1 in line 10. This stream will comprise a mixture of heavy and light components.

Where appropriate, the stream recovered from the bottom of the high pressure column 2 may optionally be passed through cooler 11. In some circumstances, where cooler 11 is present, the compressor 7 may be replaced with a pump (not shown).

Preferably the overhead temperature in the low pressure column 1 and the high pressure column 2 will be approximately the same and will be above cooling water temperature. Similarly, the bottom temperature of both columns will be approximately the same.

Figure 2:
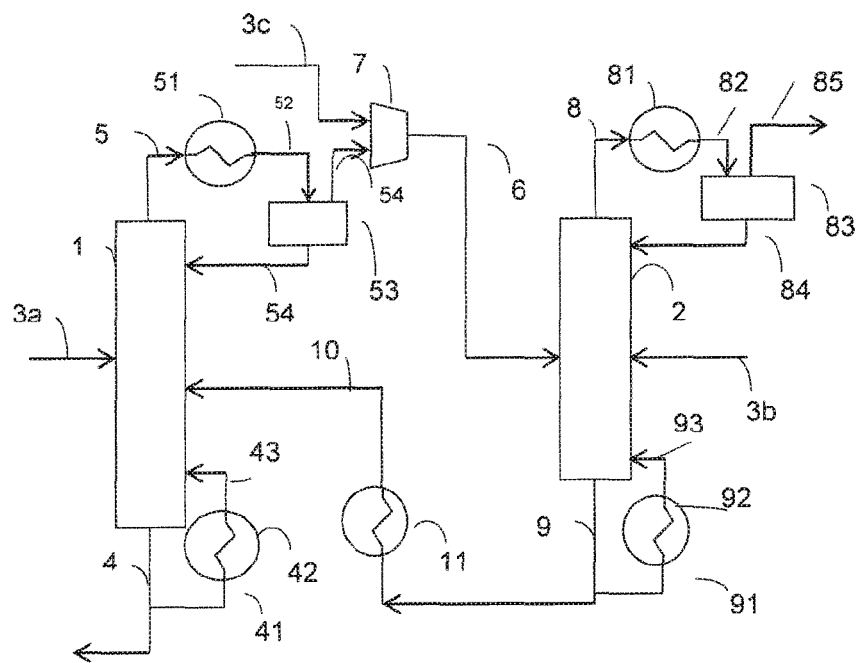
FIG. 2 is a more detailed schematic diagram of the process illustrated in FIG. 1.

One, more detailed, embodiment of the invention is illustrated in FIG. 2. As in the arrangement of FIG. 1, the feed may be supplied via one or more of lines 3a, 3b or 3c and so is added to one or both of the low pressure column 1 and the high pressure column 2. Separation will occur in both columns.

The heavy butyraldyde will be recovered from the bottom of the low pressure column 1 in line 4. A portion of that stream may be removed in line 41 and passed through reboiler 42 before being returned in line 43 to the low pressure column 1.

The stream 5 removed from the top of the low pressure column 1 in this arrangement, is passed through condenser 51 before being passed in line 52 to vapour/liquid separator 53. Liquid is returned in line 54 to the low pressure column 1. The vapour from the separator 53 is passed in line 55 to compressor 7. Where feed is added via line 3c, it may be added directly to the compressor 7 as illustrated or it may be fed into line 55. The stream from the compressor 7, which comprises a mixture of heavy and light components, is passed to the high pressure column 2.

Further separation occurs in the high pressure column 2 and the light component is recovered from the top of the high pressure column 2 in line 8 and, in this arrangement, is passed through condenser 81 before being passed in line 82 to vapour/liquid separator 83. Liquid is returned in line 84 to the high pressure column 2, The vapour from the separator is recovered in line 85.

The stream removed from the bottom of the high pressure column 2 in line 9 is passed to the low pressure column 1 in line 10. This stream will comprise a mixture of heavy and light components. A portion of stream 9 may be removed in line 91 and passed through reboiler 92 before being returned in line 93 to the high pressure column 2.

Where appropriate, the stream recovered from the bottom of the high pressure column 2 may optionally be passed through cooler 11. As in the arrangement of FIG. 1, the overhead temperature in the low pressure column 1 and the high pressure column 2 will be approximately the same and will be above cooling water temperature. Similarly, the bottom temperature of both columns will be approximately the same.

Figure 3:
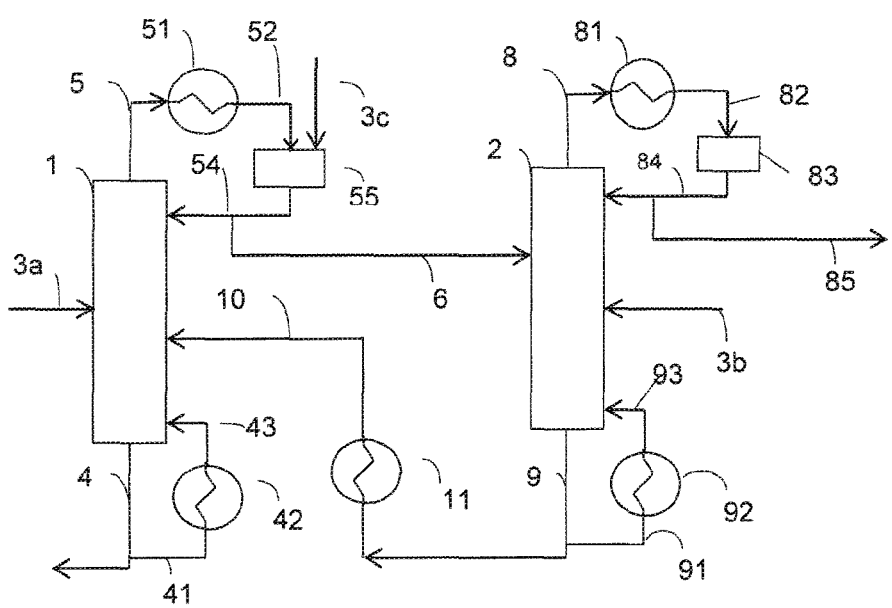
FIG. 3 is one alternative arrangement to the arrangement of the process illustrated in FIG. 2.

A modified arrangement is illustrated in FIG. 3. In this arrangement, the feed may be supplied via one or more of lines 3a, 3b and 3c and so is added to one or both of the low pressure column 1 and the high pressure column 2. Separation will occur in both columns.

The heavy butyraldyde will be recovered from the bottom of the low pressure column 1 in line 4, A portion of that stream may be removed in line 41 and passed through reboiler 42 before being returned in line 43 to the low pressure column 1.

The stream removed from the top of the low pressure column 1 in line 5, is passed through condenser 51 before a portion is returned to the low pressure column 1 in line 54. The remainder is passed to the high pressure column 2. The removal and the transfer to the high and low pressure column 1 and 2 is driven by a pump not shown.

Further separation occurs in the high pressure column 2 and the light component is recovered from the top of the high pressure column 2 in line 8. The recovered stream is passed through condenser 81 before a portion is returned to the high pressure column 2 in line 84. The remainder is recovered in line 85.

The stream removed from the bottom of the high pressure column 2 in line 9 is passed to the low pressure column 1 in line 10. This stream will comprise a mixture of heavy and light components. A portion of stream 9 may be removed in line 91 and passed through reboiler 92 before being returned in line 93 to the high pressure column 2.

Figure 4:
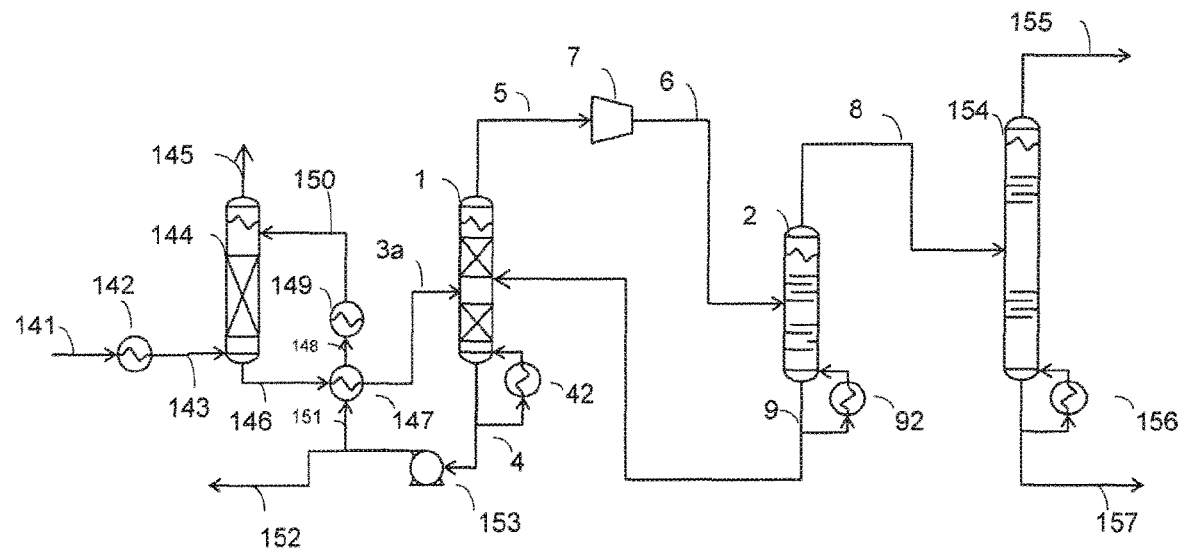
FIG. 4 is a schematic diagram of one arrangement of the process of the present invention for use in the recovery of an aldehyde from a hydroformylation reaction.

One process for treating a stream 141 recovered from a hydroformylation reaction (not shown) is illustrated in FIG. 4. In this arrangement, vent streams from different parts of the hydroformylation plant are combined, compressed and cooled in heat exchanger 142 before being fed in line 143 to a butyraldehyde scrubber 144. In one arrangement, the vent stream will be compressed to about 17.5 bars. In this arrangement, the vent stream 143 which is fed to the butyraldehyde scrubber 144 is scrubbed against butyraldehyde that is added in line 150. The stream fed in line 151 is generally free from propylene and propane since it is at least part of the aldehyde product stream recovered from the process of the first aspect of the present invention which has been passed through heat exchangers 147 and 149.

In the scrubber 144 incondensibles are separated from the stream comprising aldehyde, propylene and propane. The overhead from the butyraldehyde scrubber may be passed through a separate condenser or the condenser may be integrated with the scrubber. The condenser serves to cool to overhead to minimise butyraldehyde losses in the incondensable stream.

In the scrubber, the propylene, any propane and the butyraldehyde dissolve in the butyraldehyde scrubbing solvent whilst the majority of the incondensable components pass through the scrubber 144 and leave through an overhead vent 145.

The stream 146 recovered from the scrubber 144 is a butyraldehyde stream which is rich in propylene and optionally also propane is heated in heat exchanger 147 against butyraldehyde fed in line 151.

The stream 146, having been heated in heat exchanger 147, is passed in line 3a to the low pressure column 1 of the present invention where it is treated as discussed above in connection with FIG. 2. In one arrangement, the low pressure column 1 is operated at a pressure of 2.8 bara. In this arrangement, the low pressure column is operated at a temperature of about 108° C.

The stream recovered from the bottom of the low pressure column 1 in line 4 comprises butyraldehyde.

As discussed above, some of the butyraldehyde will be returned in line 151 to the scrubber 144. The remainder of the butyraldehyde, which is recovered in line 152 as product or is returned to the hydroformylation reaction in line 152 using pump 153 such that a constant butyraldehyde inventory is maintained in the system.

The overhead stream 5 from the low pressure column 1 may contain about 10 mol % butyraldehyde which results in a dew point of about 42° C. This stream is passed via compressor 7 and line 6 to the high pressure column 2.

The high pressure column 2 is operated at about 18 bara such that the dew point of the overhead stream 8 from the high pressure column 2 is above 42° C. In this arrangement, the stream comprises mainly propylene and propane. It will also include a small fraction of incondensables which may be up to about 7 mol %. The overhead stream 8 is generally free of butyraldehyde. The stream recovered from the bottom of the high pressure column 2 in line 9 will comprise mainly butyraldehyde but will generally also comprise about 25 mol % propylene and propane to maintain the temperature at about 110° C. This is returned to the low pressure column 1.

The overhead stream 8 from the high pressure column 2 in this arrangement is passed to an olefin/alkane splitter 154. In this splitter the propylene and propane are separated. The propylene and any remaining incondensable components are removed in line 155 and will generally be returned to the hydroformylation reactor. The propane will be removed in line 157. A reboiler 156 may be present on the olefin/alkane splitter 154.

Figure 5:
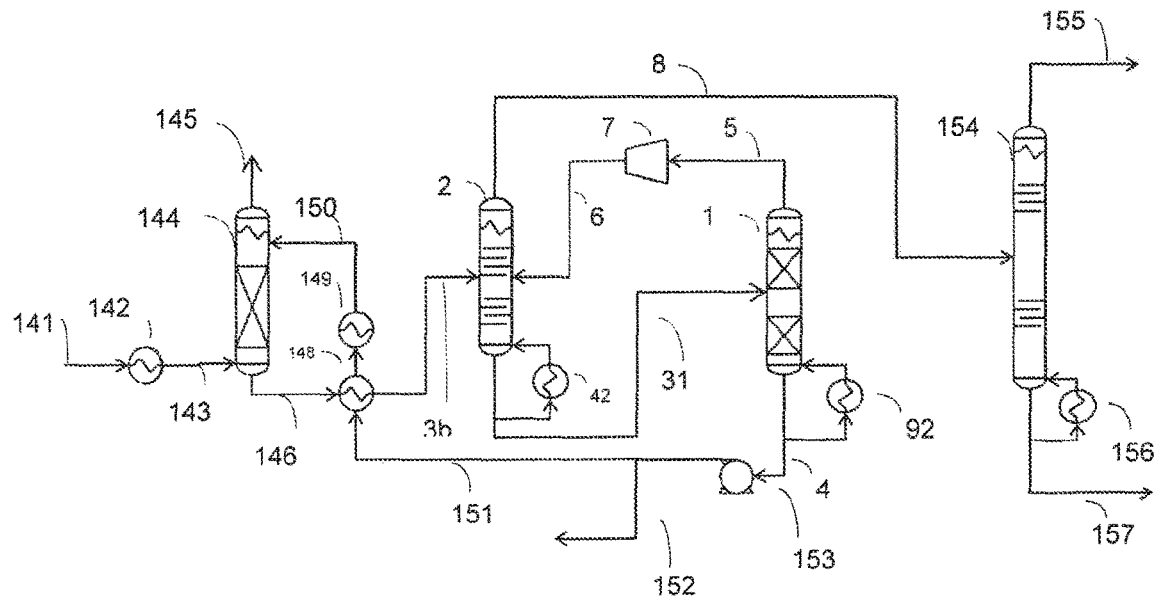
FIG. 5 is a schematic diagram of a second arrangement of the process of the present invention for use in the recovery of an aldehyde from a hydroformylation reaction.

FIG. 5 is similar to FIG. 4 in the treatment of the feed. In this process the feed is fed to the high pressure column 2 in line 3b.

Figure 6:
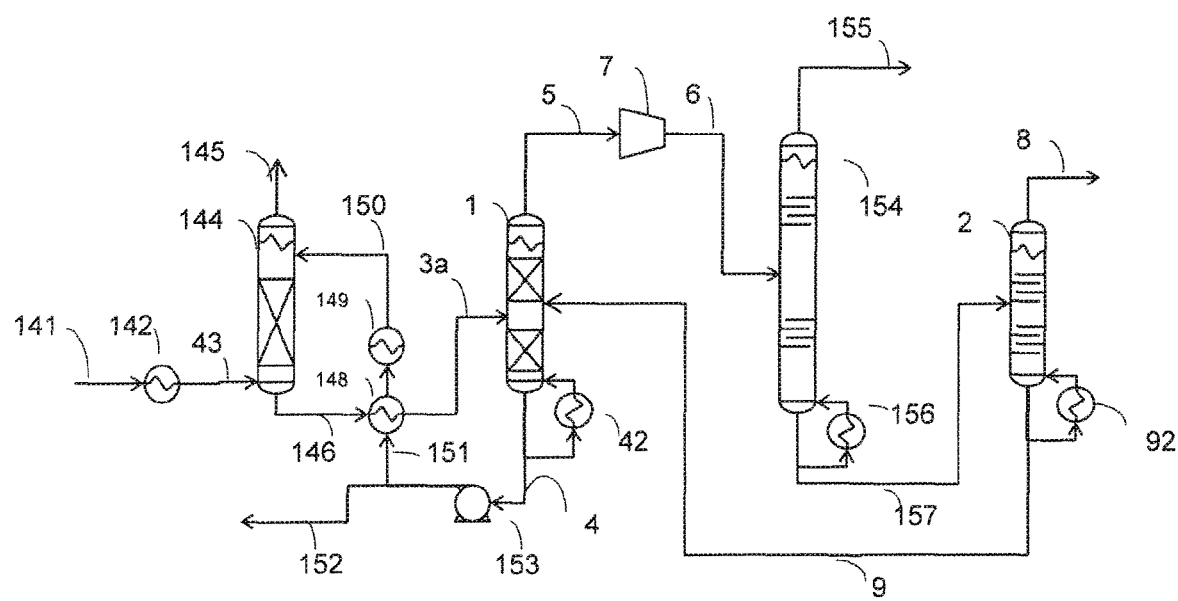
FIG. 6 is a schematic diagram of an alternative arrangement for the process of FIG. 4.

In an alternative arrangement the olefin/alkane splitter 154 may be located in the recycle loop between the low pressure column 1 and the high pressure column 2. One example of this is illustrated in FIG. 6. It will be understood that this scheme is a modification of the scheme illustrated in FIG. 4.

Thus in the arrangement illustrated in FIG. 6 the overhead stream 5 from the low pressure column 1 is passed through the compressor 7 and then passed in line 6 to the olefin/alkane splitter 154. The propylene is removed in line 155. The propane and any butyraldehyde are passed in line 157 where they are separated in the high pressure column 2. The propane is removed overhead in line 8 and the butyraldehyde is returned to the low pressure column 1 in line 9.

Whilst not illustrated a similar process in which the olefin/alkane splitter 154 is located between the high pressure column 2 and the low pressure column 1 may be provided. In this arrangement, the feed from the scrubber is sent to the high pressure column 2 as illustrated in FIG. 5.

Whilst these processes have been discussed in connection with the separation of butyraldehyde from propylene and propane, it will be understood that it is applicable to other separations. Where other separations are carried out the conditions detailed above may be altered.

In addition, the process of the present invention may be used for the separation of butyraldehyde and a dialkyl acrolein, such as ethyl propyl acrolein. Ethyl propyl acrolein is a common intermediate in the production of 2-ethylhexanol and is produced by the aldolisation of butyryladeylde. This reaction produces one mol of water per mol acrolein and thus water is commonly present in the stream passed to the separation. Both the butyraldehyde and the ethyl propyl acrolein are sensitive to temperature in that undesired heavies can be produced at elevated temperatures. It is therefore desirable to maintain the temperatures at a low level to reduce the formation of heavies whilst allowing cooling of the overhead to be achieved with cooling water at typically at about 30° C. to about 40° C.

The present invention will now be described by way of example in connection with the following examples.

Comparative Example 1 Separation of Butyraldehyde from Propylene and Propane

A mixture of 39 wt % butyraldehyde, 30 wt % propylene, 27 wt % propane, plus incondensibles is fed to a separation column. The column pressure is set at 8 bara in the top. The column generates a vapour top product containing 1 wt % butyraldehyde, 92 wt % propylene and propane, the remainder being incondesables at 15.4° C., and a liquid bottoms product containing 1 wt % propylene and propane, the remainder being butyraldehyde at 144° C. This column requires cooling medium with a lower temperature than is available from cooling water, and thus a refrigeration unit is required. The high temperature in the bottoms is likely to generate severe heavies formation of the butyraldehyde.

Example 1 Separation of Butyraldehyde from Propylene and Propane

A mixture of 85 wt % butyraldehyde, 7 wt % propylene and 6 wt % propane, the remainder being incondensable such as methane, nitrogen, CO and $H_2$, is fed to the first low pressure separation column in FIG. 1 operating at 2.8 bara. The bottoms product is liquid 99.9 wt % butyraldehyde at 108° C. whilst the top product is a vapour comprising 18 wt % butyraldehyde, 40 wt % propylene, 37 wt % propane, the remainder being incondensables. This stream is at a temperature of about 42° C. The vapour product is compressed to 18.2 bara and cooled to 56° C., resulting in a partial condensation of the stream. The compressed and cooled stream is then fed to the high pressure column which is operating at 18 bara. The top product from the high pressure column is a vapour comprising 48 wt % propylene, 45 wt % propane, and ~100 ppmwt of butyraldehyde, with the remainder being incondensables. The vapour is at a temperature of about 42° C. The bottoms product comprises 82.5 wt % butyraldehyde, 17.5 wt % propylene and propane, with virtually no incondensables being present. The bottoms product stream is at a temperature of about at 110° C. The liquid bottoms product is returned to the low pressure column to complete the recycle.

Example 2—Separation of Butyraldehyde from Propylene and Propane

A mixture of 39 wt % butyraldehyde, 30 wt % propylene, 27 wt % propane and incondensables is fed to the high pressure column of FIG. 2. This column is operating at 18 bara. Once separation has occurred, the top product is a vapour comprising 48 wt % propylene, 45 wt % propane, about 100 ppmw butyraldehyde, with the remainder being incondensables. This stream is at a temperature of about 42° C. The bottoms product from the high pressure column comprises 82.5 wt % butyraldehyde, 17.5 wt % propylene and propane, and virtually no incondensables. This stream is at a temperature of about 110° C. The liquid bottoms product is fed to the low pressure column which is operated at 2.8 bara. The bottoms product of the low pressure column is a liquid at a temperature of about 108° C. and comprises 99.5 wt % butyraldehyde, whilst the top product is a vapour 17 at a temperature of about 42° C. which comprises 18 wt % butyraldehyde, 46 w % propylene, 36 w % propane, with the remainder being incondensables. The vapour product is compressed to 18.2 bara and cooled to 56° C., resulting in a partial condensation of the stream. The compressed and cooled stream is then returned to the high pressure column to complete the recycle.

Example 3 Separation of Valeraldehyde from Butene and Butane

A mixture of 63.5 wt % valeraldehyde, 36.5 wt % butenes and butanes, and less than 0.1 wt % incondensables, is fed to a low pressure separation column operating at 1.5 bara, Once separation has taken place, the bottoms product is a liquid comprising 99.1 wt % valeraldehyde at 113° C., whilst the top product is a vapour at 45° C. comprising 9.2 wt % valeraldehyde, 90.8 wt % butenes and butanes and incondensables. The vapour product is compressed to 5.7 bara and cooled to 47° C., resulting in a partial condensation of the stream. The compressed and cooled stream is then fed to the high pressure column operating at 5.5 bara where further separation occurs. The top product from this column is a liquid at 45° C. comprising primarily butenes and butanes, with about ~3000 ppmw of valeraldehyde, and dissolved incondensables. The bottoms product stream is at 110° C. and comprises 86.5 w % valeraldehyde, 13.5 w % butenes and butanes, and substantially no incondensables. The liquid bottoms product is returned to the low pressure column to complete the recycle.

Example 4 Separation of Valeraldehyde from Butane and Butene

The same mixture as was used in Example 3 was fed to the low pressure separation column, operating at the same pressure as in Example 3, following separation a bottoms product stream of 99.1 wt % valeraldehyde, with the remainder being butane and butene was recovered. The top product stream comprised 9.1 wt % valeraldehyde, 90.8 wt % butane and butene with the rest being incondensables. This stream was at a temperature of 45° C. The vapour stream was then combined with an additional vapour stream, comprising 3.3 wt % valerladehyde, 95.9 wt % butant and butene, and incondensibles. The combined stream is compressed to 5.7 bara and cooled to 42° C., resulting in a partial condensation of the stream. The compressed and cooled stream is then fed to the high pressure column operating at 5.5 bara. Once separation has occurred in the high pressure column, a liquid top product is obtained and a vapour top product. The vapour top product contains about 50 ppmw of valeraldehyde, 96.4 wt % butane and butene, and incondensibles. This has a temperature of about 42° C. The liquid top product contains less than 0.2 wt % valeraldehyde, 99.8 wt % butene and butane, and dissolved incondensibles. The liquid bottom product contains 86 wt % valeraldehyde, 13 wt % butane and butene, and some dissolved incondensibles at 110° C. The liquid bottoms product from the high pressure separation column is returned to the low pressure separation column to complete the recycle.

Example 5 Separation of Butyraldehyde from Ethylpropylacrolein

The aldolisation of N-butyraldehyde produces one mole of water per mole of acrolein. Thus water is generally present in the separation of the butyraldehyde from ethylpropylacrolein. A further problem with this separation is that butyraldehyde and ethylpropylacrolein are likely to produce undesired heavies at elevated temperatures.

In this example, a mixture of 90 wt % butyraldehyde, 8.75 wt % ethylpropylacrolein and 1.25 wt % water is fed to the high pressure column operating at 0.4 bara. In this column, a stream of butyraldehyde and water is produced in the overheads. This stream, which is substantially free of ethylpropylacrolein, is condensed at about 47° C. A bottom stream comprising 80.3 wt % ethylpropylacrolein, 19.7 wt % butyraldehyde and 0.02 wt % water is recovered from the bottom of the high pressure column. This stream will be reboiled at 109° C. This ethylpropylacrolein rich stream then cooled to 44° C. and fed to the low pressure column, which is operating at 0.14 bara. This stream will be inserted near the top of the low pressure column. This column produces essentially pure ethylpropylacrolein in the bottoms at about 110° C. The overhead from the low pressure column, comprises about 72.5 wt % ethylpropylacrolein, 27.5 wt % butyraldehyde and 0.03 wt % water. This is then condensed. A portion of this stream is refluxed to the low pressure column and a portion is pumped to the high pressure column to complete the recycle loop. Both columns operate at a temperature in the bottom of about 110° C. and a temperature in the top at a little above 40° C. Thus cooling water temperature will be less than 40° C. is partially condensed at 47° C.

Example 6 Separation of Butyraldehyde from Ethylpropylacrolein

Example 5 was repeated with a mixture of 2.06 wt % butyraldehyde, 97.7 wt % ethylpropylacrolein and 0.22 wt % water. In this case the mixture was fed to the low pressure column, operating at 0.14 bara, A mixture of essentially pure ethylpropylacrolein is removed in the bottoms at about 110° C. A liquid overhead of a mixture of butyrylaldehyde, water and ethylpropylacrolein which comprises 82.3 wt % ethylpropylacrolein, 10.3 wt % butyraldehyde and 7.4 wt % water. This is condensed at 52° C. This is part refluxed and part pumped to the high pressure column which is operating at about 0.4 bara. In this column, a stream comprising butyraldehyde and water and which is essentially free of ethylpropylacrolein is recovered in the overheads. This overhead stream is part refluxed and part removed for further processing. A bottoms stream comprising a mixture of 3.7 wtl% butyrylaldehyde, 7.3 wt % water and 89 wt % ethylpropylacrolein is reboiled at 110° C. Part of this stream is cooled to 90° C. and returned to the low pressure column thereby completing the recycle loop and an ethylproplyacrolein rich stream is recovered in the bottoms. This stream, which is at about 110° C. contains about 63 mol % ethylpropylacrolein. This ethylpropylacrolein rich stream is returned to the low pressure column.

Example 7 Separation of Butyraldehyde from Ethylpropylacrolein

Example 5 was repeated except that the butyraldehyde and water recovered as overhead from the high pressure column is separated into a water rich stream and a butyraldehyde rich stream. The butyraldehyde rich stream is used to provide reflux to the high pressure column.

Example 8 Separation of Valeraldehyde from Propylbutylacrolein

The aldolisation of valeraldehyde produces one mole of water per mole of acrolein. Thus water is generally present in the separation of the valeraldehyde from propylbutylacrolein. A further problem with this separation is that valeraldehyde and propylbutylacrolein are likely to produce undesired heavies at elevated temperatures.

In this example, a mixture of 90 mol % valeraldehyde, 5 mol % water and 5 mol % propylbutylacrolein is fed to the high pressure column operating at 0.4 bara. In this column, propylbutylacrolein free valeraldehyde/water is produced in the overheads at about 41° C., while a propylbutylacrolein rich stream is produced in the bottoms at a temperature of about 80° C. This bottoms stream contains about 91 mol % propylbutylacrolein and 6.5 mol % valeraldehyde and 2.5 mol % water. This propylbutylacrolein rich stream is fed to the low pressure column, which is operating at 0.08 bara. This column produces essentially pure propylbutylacrolein in the bottoms at about 80° C. The overhead, comprising about 92 mol % propylbutylacrolein, valeraldehyde and water, is partially condensed at 40° C. The liquid from the condenser is returned as reflux to the low pressure column, whilst the vapour is compressed and returned to the high pressure column.

Example 9 Separation of 2-Methylbutyraldehyde from Propylbutylacrolein

A mixture of 3.5 mol % 2-methylbutyraldehyde, 1.5 mol % water and 95 mol % propylbutylacrolein is fed to the low pressure column operating at 0.08 bara. In this column, essentially pure propylbutylacrolein rich stream is produced in the bottoms at a temperature of about 80° C. This overhead stream is partially condensed at about 40° C. The liquid from the condenser is returned as reflux to the low pressure column whilst the vapour is compressed and fed to the high pressure column which operates at 0.25 bara. In this high pressure column, a 2-methylbutyraldehyde/water mixture is produced in the overhead at about 40° C. A stream comprising about 65 mol % propylbutylacrolein, 35 mol % 2-methylbutyraldehyde and virtually no water is recovered from the bottoms at 80° C. This stream is returned to the low pressure column.

Example 10 Separation of Propionaidhyde from Ethylene

A mixture of 44.8 wt % propionaldehyde, 28.3 wt % ethylene, 26.8 wt % ethane, and less than 0.1 wt % incondensables is fed to the low pressure column operating at 5.0 bara. A bottom liquid stream is recovered comprising over 99.9 wt % propionaldehyde at 103° C. whilst the top product is a vapour comprising 33.7 wt % propionaldehyde, 32.1 wt % ethylene, 34.1 wt % ethane and incondensables at a temperature of 47° C. This product stream is compressed to 50 bara and cooled to 50° C. resulting in a partial condensation of the stream. This stream is then fed to the high pressure column operating at 48.5 bara. The top product stream from the high pressure column is a vapour comprising primarily ethylene and ethane and less than 1000 ppmw of propionaldehyde and dissolved in condensables at 16° C.

The stream recovered from the bottom of the high pressure column comprises 76.5 wt % propionaldehyde, 7.8 wt % ethylene, 15.7 wt % ethane and virtually no incondensables. This stream, which is at a 102° C. is returned to the low pressure column to complete the recycle loop.

The overheads temperature in the high pressure column is only 16° C. which it will be understood in some cases is below the temperature of the cooling water and thus will require alternative cooling.

The invention claimed is:

1. A process for the separation of an aldehyde and a second component from a feed stream comprising the aldehyde and the second component, said process comprising:
   (a) providing the feed stream to one or both of a first separation vessel operating at a first pressure and a second separation vessel operating at a second pressure wherein said second pressure is greater than said first pressure;
   (b) operating said first separation vessel and said second separation vessel such that separation occurs;
   (c) recovering an aldehyde product stream from at or near the bottom of the first separation vessel, said aldehyde product stream having a concentration of aldehyde which is higher than that in the feed stream;
   (d) recovering a second component stream from at or near the top of the second separation vessel, said second component stream having a concentration of second component which is higher than in the feed stream;
   (e) removing a first recycle stream from at or near the top of the first separation vessel and feeding it to the second separation vessel; and
   (f) removing a second recycle stream from at or near the bottom of the second separation vessel and feeding it to the first separation vessel.

2. A process according to claim 1 wherein the second component is an olefin.

3. A process according to claim 2 wherein the olefin is the olefin from which the aldehyde has been formed.

4. A process according to claim 3 wherein:
   the aldehyde is butyraldehyde and the second component is propylene with propane optionally being present;
   the aldehyde is valeraldehyde and the second component is butylene with butane optionally being present; or
   the aldehyde is propionaldehyde and the second component is ethylene with ethane optionally being present.

5. A process according to claim 1 wherein the second component is an unsaturated aldehyde.

6. A process according to claim 5 wherein the unsaturated aldehyde is a $C_3$ to $C_{20}$ unsaturated olefin.

7. A process according to claim 5 wherein:
   the aldehyde is butyraldehyde and the second component is ethylpropylacrolein;
   the aldehyde is valeraldehyde and the second component is propylbutylacrolein; or
   the aldehyde is 2-methylbutyraldehyde, 3-methylbutyrylaldehyde or both 2-methylbutyrylaldehyde and 3-methylbutyrylaldehyde and the second component is propylbutylacrolein.

8. A process according to claim 1 wherein the first and second separation vessels are flash vessels with associated feed condensers.

9. A process according to claim 1 wherein the first and second separation vessels are separation columns.

10. A process according to claim 1 wherein the first separation vessel is operated at a vacuum of from about 1 mbara to about 50 mbara.

11. A process according to any claim 1 wherein the first separation vessel is operated at a pressure of from about 0.05 bara to about 10 bara.

12. A process according to claim 1 wherein the second separation vessel is operated at a pressure below the critical pressure of material therein.

13. A process according claim 1 wherein the first recycle stream is passed through one or more compressors before it is fed to the second separation vessel.

14. A process according to claim 1 wherein the lower portion of the first separation vessel is operated at a temperature of about 50° C. to about 200° C.

15. A process according to claim 1 wherein the lower portion of the second separation vessel is operated at a temperature of 50° C. to about 200° C.

16. A process according to claim 1 wherein the pressure of the second separation vessel is selected such that the temperature of the stream taken at or near the bottom portion of the second separating vessel is within about 20° C. of the temperature of a bottom portion of the first separating vessel.

17. A process according to claim 1 wherein the stream recovered from at or near the top of the second separation vessel is passed to a further separation means.

18. A process according to claim 1 wherein the stream recovered from at or near the top of the first separation vessel is passed through a further separation means before it is passed to the second separation vessel.

19. A process for carrying out the hydroformylation of an olefin wherein one or more vent streams from a hydroformylation reaction is treated in accordance with the process according to claim 1.

20. A process according to claim 19 wherein the one or more vent streams are treated in an aldehyde scrubber against a stream which is substantially free of olefin.

* * * * *